United States Patent [19]
Timerdahl et al.

[11] Patent Number: 4,863,379
[45] Date of Patent: Sep. 5, 1989

[54] VALVE ARRANGEMENT FOR HAND-OPERATED DENTAL TOOLS

[76] Inventors: Ake Timerdahl, Torsbyvägen 20, S-139 00, Värmdö ; Jan Angseryd, Oldlingsvägen 59, S-138 00, Alta, both of Sweden

[21] Appl. No.: 191,026

[22] Filed: Apr. 28, 1988

Related U.S. Application Data

[63] Continuation of Ser. No. 858,930, May 2, 1986, abandoned.

[51] Int. Cl.⁴ ................................................. A61C 1/02
[52] U.S. Cl. ......................................... 433/28; 433/98
[58] Field of Search ..................................... 433/28, 98

[56] References Cited

U.S. PATENT DOCUMENTS

| | | | |
|---|---|---|---|
| 3,742,606 | 7/1973 | Fleer et al. | 433/28 |
| 3,959,882 | 6/1976 | Rackson | 433/98 |
| 3,982,322 | 9/1976 | Fleer | 433/28 |
| 4,375,963 | 3/1983 | Betush | 433/28 |
| 4,450,862 | 5/1984 | Hogan | 137/595 |

FOREIGN PATENT DOCUMENTS

| | | |
|---|---|---|
| 0023672 | 2/1981 | European Pat. Off. . |
| 0042269 | 12/1981 | European Pat. Off. ............. 433/28 |
| 3225794 | 1/1984 | Fed. Rep. of Germany ........ 433/28 |
| 1012565 | 12/1965 | United Kingdom . |
| 2051378 | 1/1981 | United Kingdom . |

*Primary Examiner*—John J. Wilson
*Attorney, Agent, or Firm*—Young & Thompson

[57] ABSTRACT

The invention relates to a valve arrangement for controlling the flow of pressurized air, water and/or other media to at least one hand-operated tool, preferably an instrument for dental work. The valve arrangement includes for each tool a valve for each medium. According to the invention, each valve comprises a first valve part and a second valve part, those valve parts being arranged for relative movement between an open and a closed psoition under the influence of actuating means and further comprises a flexible hose connected at respective ends to the two first and second valve parts. When the valve parts occupy their valve-closed position, the part of the hose located between the two valve parts is folded so as to exhibit a flow-inhibiting fold or kink, whereas when the valve parts occupy their valve-open positions the flow-inhibiting fold is no longer present in the hose.

3 Claims, 2 Drawing Sheets

VALVE ARRANGEMENT FOR HAND-OPERATED DENTAL TOOLS

This application is a continuation of application Ser. No. 858,930, filed 5/2/86, now abandoned.

The invention relates to a valve arrangement for controlling the supply of pressurized-air, water and/or other media to at least one hand-operated tool, preferably an instrument for dental work, which valve arrangement includes for each tool a valve for each medium.

Valve arrangements of this kind are known to the art, for example for use in appliances for dental work. Such appliances normally incorporate a plurality of mutually different tools or instruments, which are used singly, one at a time. Normally, each instrument must be supplied with air under pressure and/or water and possibly other media. All instruments are placed in a holder when not in use, and the holder is provided with means that ensures that only an instrument which has been removed from its holder can be set into operation.

Such prior art appliances require an extremely large number of valves for controlling the flow of different media to the various instruments, thereby rendering the appliance complicated, expensive and bulky.

The object of the present invention is to provide a valve arrangement of the aforesaid kind which is of simple construction and inexpensive to manufacture, and which is also reliable in use. This is achieved in accordance with the invention in that each valve includes a first valve part and a second valve part which under the influence of an actuated means can be moved relative to one another between a valve-open position and a valve-closed position, and further includes a flexible hose which connects the two valve parts together and which, in the closed position of the valve parts, is folded at the part thereof located between the valve parts, such that said hose part exhibits therein a fold or kink sufficient to inhibit the flow of medium through said hose part, while when the valve parts occupy their open position the hose part is free from said flow-inhibiting fold.

BRIEF DESCRIPTION OF THE DRAWINGS

The invention will now be described with reference to the accompanying drawing, in which.

DETAILED DESCRIPTION OF THE INVENTION

Figure 1:
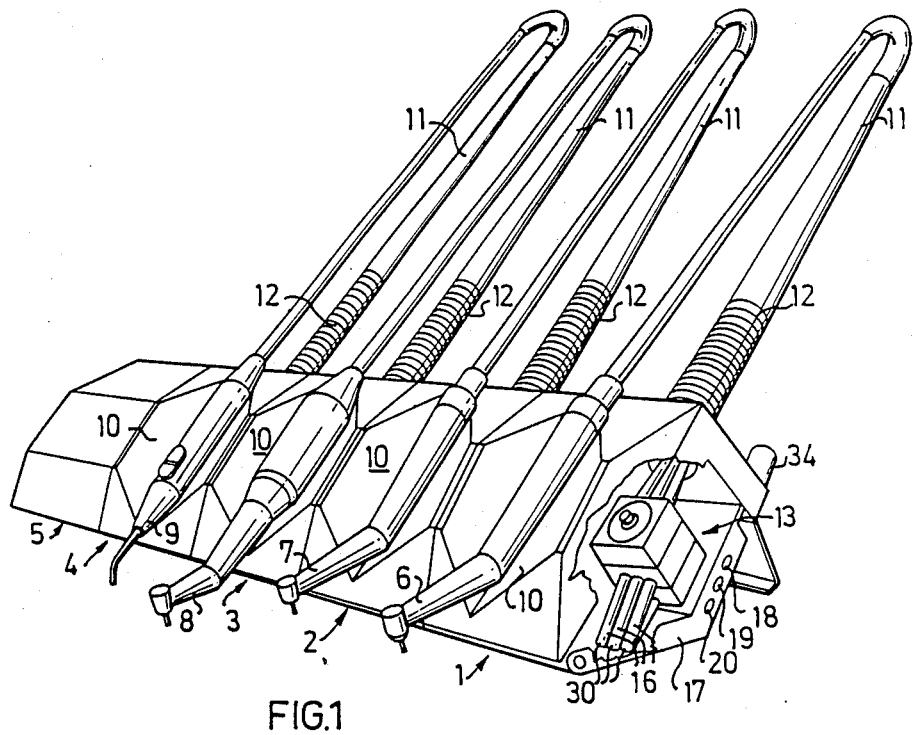
FIG. 1 is a partially cut-away perspective view of a dental appliance which incorporates a plurality of tools or instruments for dental work and which is equipped with a valve arrangement according to one embodiment of the invention.

FIG. 1 illustrates a dental appliance, which is provided with a valve arrangement according to the invention. The dental appliance comprises five blocks or assemblies 1-5, which are of uniform size and incorporated with each other. Each of the blocks 1-4 is provided with an individual hand-operated instrument 6-9, whereas the block 5 may incorporate various types of control devices, these devices having no direct connection with the present invention. As will be understood, the blocks may vary in number, in accordance with the number of instruments provided.

In FIG. 1, each instrument 6-9 is shown in an inoperative position, the instrument being located in a holder in a respective block 1-4. In this embodiment, the holder has the form of a substantially V-shaped recess 10 in the inclined upper surface of the block. Each instrument 6-9 is connected to its respective block 1-4 through a pipe 11 incorporating channels for the flow of pressurized air, water and/or other media to the instrument, and optionally also a line for supplying electric current to said instrument. The pipe 11 may be of a kind known per se, and is conveniently provided with a spring-biased part 12 nearest respective blocks 1-4 and a flexible part nearest respective instruments 6-9.

The block 1 shown in FIG. 1 has been partially cut away, so as to illustrate the valve arrangement located therein. The valve arrangement 13 is shown more clearly in FIGS. 2 and 3, each of which illustrates the block in cross-section, with the valve parts of the arrangement in their respective closed and open positions.

Figure 2:
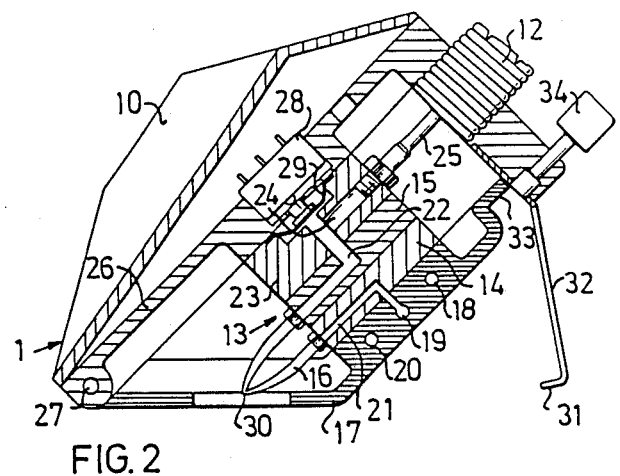
FIG. 2 is a cross-sectional view of the valve arrangement illustrated in FIG. 1, with the valve parts shown in their closed position.

FIG. 2 illustrates the valve arrangment 13 in its closed position. The valve arrangement of the FIG. 1 embodiment comprises three separate valves, and the cross-sectional view of FIG. 2 is taken through one of these valves. The valve illustrated in FIG. 2 includes a first valve part 14, a second valve part 15, and a flexible hose 16 joining the two valve parts 14 and 15. The first valve part 14 is connected firmly to a base part 17, which forms a stationary part of the block 1 and has incorporated therein three channels 18, 19 and 20 through which pressurized air, water and optionally other media can be passed from sources not shown. As shown in FIG. 2, the first valve part 14 is provided with a channel 21, which is connected to the channel 19 and to the hose 16, the other end of which hose 16 is connected to a channel 22 in the other valve part 15. The other valve part 15 is connected firmly to an intermediate member 23 which incorporates a channel 24, to which the channel 22 is connected. In turn, the channel 24 opens into a hose 25, which extends through the spring-biased part 12 and the pipe 11, and is connected to the instrument 6.

The intermediate member 23, and therewith also the second valve part 15, is firmly mounted on an auxiliary component 26, which is pivotally connected to the base part 17 by a shaft or pivot pin 27. The auxiliary component 26 also carries the instrument holder 10 and the spring-biased part 12 of the pipe 11. In the embodiment illustrated in FIGS. 2 and 3, the auxiliary component 26 also carries a switch 28, which through the action of a diaphragm 29 is actuated by the pressure in the channel 24, to enable electric current to flow to the instrument in response to the pressure prevailing in the channel 24. In this case, an electric conductor extends from the switch 28 to the instrument. This electric conductor is not shown in the drawing, but can obviously be located in the pipe 11.

As shown in FIG. 2, in which the valve parts 14 and 15 occupy their valve-closed positions, i.e. are located close to one another, the hose 16 in this valve mode exhibits an abrupt fold or kink 30, which prevents the flow of medium through the hose 16 from the channel 21 in the first valve part, to the channel 22 in the second valve part 15.

Figure 3:
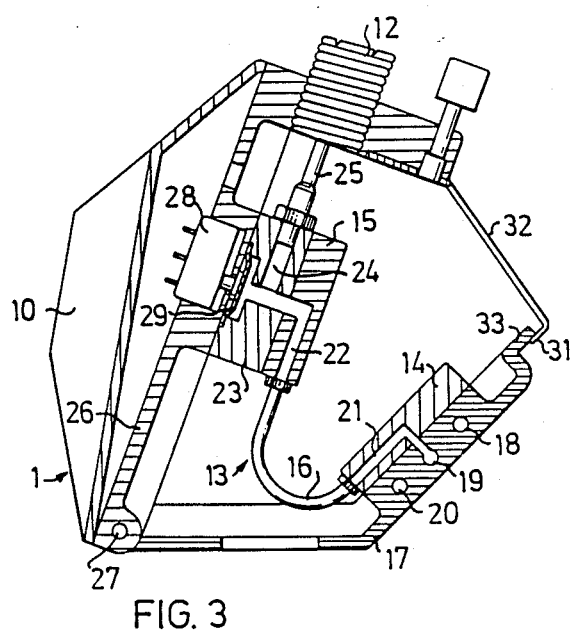
FIG. 3 is a cross-sectional view similar to that of FIG. 2, but showing the valve parts in their open position.

In the position illustrated in FIG. 3, the auxiliary component 26 has swung anti-clockwise from the position illustrated in FIG. 2. This rotation of the auxiliary component takes place when the instrument or tool 6 is lifted from its holder 10 and pulled forward to its working position, these actions causing the pipe 11 and the spring-biased part 12 thereof to be subjected to forces which cause the auxiliary component 26 to swing in the aforesaid manner. This swinging or rotary movement of the auxiliary component 26 is restricted through the agency of a bent end-part 31 which is located on a limiting device 32 extending outwardly from the auxiliary component 26 and which is brought into abutment with a projection 33 on the base part 17.

When the auxiliary component 26 is swung rearwardly to the position illustrated in FIG. 3, the second valve part is moved away from the first valve part 14. This also causes the ends of the hose 16 to move away from one another, causing the hose to straighten to an extent such as to remove the fold or kink 30. Pressure medium can now flow from the channel 19 through the channel 21 and the now open hose 16, and also through the channels 22 and 24 to the hose 25, for the supply of medium to the instrument. Thus, when the valve arrangement occupies the position illustrated in FIG. 3, there is nothing to prevent the pressure medium from flowing therethrough, meaning that the valve comprising the valve parts 14,15 and the hose 16 is open.

As will be understood from the aforegoing, the hose 16 forms the actual valve body for opening and closing the valve according to the invention, the valve being closed by bending the hose to form therein a sharp fold or kink 30. The valve is opened by straightening the hose 16 sufficiently to remove the fold 30. In the illustrated embodiment, the movements between closed and open positions are effected under the influence of the forces occurring in the pipe 11 when the instrument concerned is lifted from its holder 10. Consequently, pressure medium will only flow to the instrument when it is lifted from its holder. In some cases, however, it may be desired to lift the instrument from its holder 10 without setting the instrument in function. This can be the case when changing or replacing instruments for example. To this end, the auxiliary component 26 is provided with a catch means 34, which can be placed manually behind the projection 33 on the base part 17 when the auxiliary component 26 occupies the position shown in FIG. 2, i.e. when the valve is closed.

It will be understood that the invention is not restricted to the aforedescribed embodiment, and that modifications can be made thereto within the scope of the following claims.

We claim:

1. A valve arrangement for controlling the supply of pressurized fluid to at least one hand-operated tool, comprising:
    at least one hand-operated tool supplied with pressurized fluid;
    a base having at least one conduit adapted to be connected to a source of pressurized fluid;
    at least one member pivotally mounted on said base, having at least one conduit in fluid communication with a said at least one hand-operated tool, each said at least one member extending upwardly relative to said base;
    and a flexible hose interconnecting a said at least one conduit of said base and a said at least one conduit of a said at least one member;
    each said at least one member being pivotally movable relative to said base about a horizontal axis extending transversely of said flexible hose from a first supported position in which said base supports said at least one member, and said flexible hose is caused to be folded rearwardly upon itself thus blocking passage of fluid therethrough, to a second forwardly disposed position in which said flexible hose is caused to be extended forwardly so as to be unconstricted and permit flow of fluid therethrough;
    each said at least one hand-operated tool being connected to a said at least one member a distance from said axis such that forward movement of said tool to a working position pulls said at least one member forward and placement of said tool on said at least one member during non-use urges said member rearwardly into supported relationship on said base.

2. Valve arrangement according to claim 1, wherein said at least one member comprises a pressure sensor actuating a switch, responsive to pressure sensed in said at least one conduit of said at least one member.

3. Valve arrangement according to claim 1, and catch means for maintaining said at least one member in its first supported position relative to said base.

* * * * *